United States Patent [19]
Alonso et al.

[11] Patent Number: 5,882,688
[45] Date of Patent: Mar. 16, 1999

[54] COMPOSITION FOR THE PROTECTION OF FRESH SEA FOOD FROM MELANOSIS AND METHOD THEREFORE

[75] Inventors: Eduardo G. Alonso; Normando Rogert; Salvador P. Florio; Hector E. Panzarasa, all of Buenos Aires, Argentina

[73] Assignee: Adital, S.A., Buenos Aires, Argentina

[21] Appl. No.: 858,157

[22] Filed: Apr. 11, 1997

[51] Int. Cl.⁶ ............................ A61K 31/19; A61K 33/04
[52] U.S. Cl. ........................... 424/711; 426/321; 514/474; 514/562; 514/574
[58] Field of Search ..................... 514/562, 574, 514/474; 424/711; 426/321

[56] References Cited

U.S. PATENT DOCUMENTS 4,476,112  10/1984  Aversano .................................. 426/127

OTHER PUBLICATIONS

Kirby, WO 9617899, 1996.

*Primary Examiner*—Leonard Schenkman
*Attorney, Agent, or Firm*—Staas & Halsey

[57] ABSTRACT

A composition to be applied in the preservation of edible sea products exposed to melanization is disclosed; said composition being composed of potassium or sodium bisulfite, organic acids acceptable from the alimentary point of view, such as citric acid or tartaric acid and acid salts of the same, ascorbic acid or its salts and L-cysteine or N-acetyl-cysteine as an enzymatic inhibitor, antioxidant, sequestrate.

20 Claims, No Drawings

COMPOSITION FOR THE PROTECTION OF FRESH SEA FOOD FROM MELANOSIS AND METHOD THEREFORE

BACKGROUND OF THE INVENTION

Melanin is a natural pigment, widely spread in the animal and vegetal kingdoms, its color varying from a deep black to a reddish brown, with many intermediate tints. Said melanin gathers in the cells at the areas in the body that are exposed to ultraviolet radiation, and forms solar screens or filters for the protection of the anatomic structures underneath.

Melanin is present in the shape of micropellets and is a product of the metabolic degrading of phenilanin, tyrosine, dehydroxiphenilanin, 5,6-quinine and 5,6-dihyroxindole-2-carboxilic acid (cumelanine).

The melanin gathered in the melanocytes of the skin, being especially found on fish, forms stains or dark surfaces more or less extended in areas which may also be part of mimetic systems. This combination of different functions of melanin (solar protection - mimetism) occurs in the sea fauna in the water near the surface, such as crustaceans (spiny lobster, prawns, crayfish).

This class of invertebrates have a slight shadowy shade, due to the melanin micropellets distributed in the teguments and shell. Out of their habitat, they acquire a dark tint that stresses as they remain in the environmental air. This process, named melanization, or melanogenesis, is due to oxidation that can be enzymatic due to condensation and polymerization of aminoacid and protein groups, or else non-enzymatic due to the formation of metallic chelates with copper and iron, of the forerunners of melanin, present in the tissues, with which the content of melanin in the same increases, thus stressing the darkening.

In conventional practice, this oxidation and darkening process is controlled, up to a certain extent, by the storage of the products at low temperatures, in cold storage chambers or, given the case, maintaining the collected products in alternate layers or in bulk with ice. This method only slows down or delays the melanization process, which is undesirable, since the darkening is a clear sign for the consumers that a preserved product is deficient and/or has been stored for a long time.

It has been proved that it is now possible to extend the preservation of sea products, subject to melanization or darkening of the body out of their habitat, especially crustaceans such as shrimp, spiny lobsters, crayfish, kril, crabs, etc. This is possible by applying a composition in which a microbicidal system and a reducing agent fuse, both being specific, and also compatible from the alimentary point of view.

BRIEF DESCRIPTION OF THE INVENTION

It is an object of this invention to provide a compound which is useful to improve the preservation of fresh sea products or preserved in cold conditions, being exposed to melanization, especially crustaceans. Said compound characterized because it includes 8–15% of sodium or potassium bisulfite, 1–5% of ascorbic acid or its salts, from 1 to 8% citric or tartaric acid or their salts and 0,2 to 0,8% of L-cysteine or N-acetyl-cysteine, being the rest to 100 an inert carrier. Said amounts being gravimetric percentages for each 100 g of compound.

It is another object of this invention to improve the preservation of fresh sea products or stored in cold conditions, subject to melanization, such as crustaceans, a compound being characterized because it includes: 11% sodium or potassium bisulfite, 5% of citric acid or tartaric acid or their salts, 2% of ascorbic acid or its salts, 0,4 of L-cysteine or N-acetyl-Cysteine and the rest to 100, sodium chloride as an inert carrier. Those values being gravimetric percentages for each 100 parts per weight of compound.

It is also an object of the invention to provide an aqeous solution which, being applied through the immersion of sea products in said solution, especially fresh crustaceans or the same stored under cold conditions, is characterized because it includes the mentioned system or compound already mentioned diluted in a gravimetric ratio of 1/10 to 1/20 with salt or fresh water.

DETAILED DESCRIPTION OF THE INVENTION

The compound of the present invention introduces an important innovation in the art of the preservation of edible sea products, because it makes it possible to extend the preservation of those products exposed to melanization, inhibiting or delaying the natural mechanism leading from the darkening of the tissues to the loosening of the side enzymatic processes that lead to the slackening or laxity of the tissues (which goes before the pre-agonic rigidity, followed by the lysis or autodigestion of the tissues). In the manifestation and development of these processes, the microbial activity is also incident due to the bacterial flora of the environment and the internal bacterial flora.

The preservation of captured sea products, according to the present invention, shrimps, spiny lobster, crayfish, crabs etc., may be carried out acting directly on the catch through immersion in solutions formulated with the already mentioned compound and in the set gravimetric percentages, dissolved in water to 5 to 8% in weight. The practice has shown that a kilogram of the compound object of this invention, dissolved in 20 liters of salt or fresh water, is enough to prevent the melanization 25 kg of of crustaceans, of that solution applied through immersion at temperatures of 0°–1° C.

The mentioned inert carrier of the elements composing the compound of this invention may be any soluble substance compatible from the alimentary point of view, and also due to its capacity to keep the organoleptic characteristics and the texture of the catch under treatment. Table salt is advisable concerning this aspect due to its cost and availability, which, obviously, does not exclude the possibility of using other salts or soluble compounds, as citrates, tartrates, etc. Sodium or potassium bisulfite acts as an inhibitor of melanization, as well as a biocidal agent. As such, it acts to inhibit the bacterial spread by the slow and continuous dispensation of sulfur dioxide, taking into account the mention acid/base between potassium or sodium bisulfite and the acid compound (citric, etc.). On the other hand, it is a reducing agent in an acid means, due to which it also acts as an inhibitor of natural enzymatic processes.

The reducing effect of bisulfite adds to the redox properties of the ascorbic acid, already known, borne by the acid means produced due to the disassociation of the citric or tartaric acid and from the combination of these elements a means incompatible with the polymerization of the forerunners of melanin being formed as well as the inhibition of the darkening process of the catches.

The L-cysteine or N-acetyl-cysteine acts as a reducing agent and is a copper sequestrate. Moreover, it acts as a specific inhibitor of Dopa-Oxidasa, being these effects of great importance in the prevention of melanogenesis.

| | |
|---|---|
| Sodium bisulfite | 110 g |
| Citric Acid | 50 g |
| Ascorbic Acid | 20 g |
| L-cysteine | 6 g |
| Sodium chloride | 814 g |

Afterwards dissolved in 20 liters of running tap water.

With this solution cooled to 0°/0,5° C., two loads of 22 kg (one of shrimps and the other of whole middle-sized crayfish) were put under treatment in a cold storage chamber at a controlled temperature of 0°–1° C. The products were put in two perforated stainless steel barrels which were submerged in the above-mentioned solution.

The loads thus treated, maintained in the mentioned conditions, were inspected at intervals of 12 hours during four running days. No changes being observed in the color of the products, nor in the texture, consistency nor organoleptic characters of the treated products.

In a control load of the same origin and treated in the same way, without the aid of the preserving solution, a gradual darkening occurred on the catches as from the first 24 hours, the same extending from the cervical part through the exoskeleton and the ventral part, being completed after the second day with telson and uropods.

The compound according to the present invention may be formulated in unit containers in which all the elements duly dosified are collected.

We claim:

1. An aqueous composition to preserve fresh sea products, comprising:

8–15 wt % sodium or potassium bisulfite;

1–5 wt % ascorbic acid or salts thereof;

1–8 wt % citric or tartaric acid, or salts thereof; and 0.2 to 0.8 wt % L-cysteine or N-acetyl-cysteine.

2. A composition to preserve fresh sea products according to claim 1, wherein the composition comprises 8–15 wt % sodium or potassium bisulfite, 1–5 wt % ascorbic acid or salts thereof, 1–8 wt % citric or tartaric acid, or salts thereof and 0.2 to 0.8 wt % L-cysteine or N-acetyl-cysteine with the remainder being sodium chloride.

3. A composition to preserve fresh sea products according to claim 1, wherein the composition comprises 11 wt % sodium or potassium bisulfite, 2 wt % ascorbic acid or salts thereof, 5 wt % citric or tartaric acid, or salts thereof and 0.4 wt % L-cysteine or N-acetyl-cysteine.

4. A composition to preserve fresh sea products according to claim 1, wherein the composition contains sodium bisulfite.

5. A composition to preserve fresh sea products according to claim 1, wherein the composition contains potassium bisulfite.

6. A composition to preserve fresh sea products according to claim 1, wherein the composition contains citric acid or salts thereof.

7. A composition to preserve fresh sea products according to claim 1, wherein the composition contains tartaric acid or salts thereof.

8. A composition to preserve fresh sea products according to claim 1, wherein the composition contains L-cysteine.

9. A composition to preserve fresh sea products according to claim 1, wherein the composition contains N-acetyl-cysteine.

10. A method for preserving fresh sea products, comprising immersing said sea products in an aqueous solution of a composition comprising:

8–15 wt % sodium or potassium bisulfite;

1–5 wt % ascorbic acid or salts thereof;

1–8 wt % citric or tartaric acid, or salts thereof; and 0.2 to 0.8 wt % L-cysteine or N-acetyl-cysteine diluting the composition with water; and 11. A method of preserving fresh sea products according to claim 10, wherein the composition is diluted with fresh water.

12. A method of preserving fresh sea products according to claim 10, wherein the composition is diluted with salt water.

13. A method of preserving fresh sea products according to claim 10, wherein the sea products are placed in perforated containers then immersed in the aqueous solution.

14. A method of preserving fresh sea products according to claim 10, wherein the sea products are crustaceans.

15. A method of preserving fresh sea products according to claim 10, wherein the composition comprises:

8–15 wt % sodium or potassium bisulfite,

1–5 wt % ascorbic acid or salts thereof,

1–8 wt % citric or tartaric acid, or salts thereof and 0.2 to 0.8 wt % L-cysteine or N-acetyl-cysteine with the remainder being sodium chloride.

16. A method of preserving fresh sea products according to claim 10, wherein the composition comprises 11 wt % sodium or potassium bisulfite, 2 wt % ascorbic acid or salts thereof, 5 wt % citric or tartaric acid, or salts thereof and 0.4 wt % L-cysteine or N-acetyl-cysteine.

17. A method of preserving fresh sea products according to claim 10, wherein the composition contains sodium bisulfite.

18. A method of preserving fresh sea products according to claim 10, wherein the composition contains potassium bisulfite.

19. A method of preserving fresh sea products according to claim 10, wherein the composition contains citric acid or salts thereof.

20. A method of preserving fresh sea products according to claim 10, wherein the composition contains tartaric acid or salts thereof.

* * * * *